United States Patent
Astatke et al.

(10) Patent No.: US 11,199,544 B2
(45) Date of Patent: Dec. 14, 2021

(54) PRE-SYMPTOMATIC DIAGNOSIS OF A VIRAL ILLNESS

(71) Applicant: The Johns Hopkins University, Baltimore, MD (US)

(72) Inventors: Mekbib Astatke, Gaithersburg, MD (US); Allyson M. Bissing-Gibson, Columbia, MD (US); Rachel S. Quizon, Olney, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 16/354,238

(22) Filed: Mar. 15, 2019

(65) Prior Publication Data

US 2020/0292545 A1 Sep. 17, 2020

(51) Int. Cl.
*G01N 33/569* (2006.01)
*C12N 7/00* (2006.01)

(52) U.S. Cl.
CPC ......... *G01N 33/56983* (2013.01); *C12N 7/00* (2013.01); *G01N 2800/26* (2013.01)

(58) Field of Classification Search
CPC ............ A61K 39/12; A61K 2039/5256; A61K 2039/53; A61K 39/00; C12N 15/86; C12N 2770/36134; C12N 2770/36143; C12N 2710/10043; C12N 15/111; C12N 15/85; C12N 2760/14222; C12N 2770/20021; Y02A 50/387; C12Q 1/70; C12Q 2545/10; C12Q 2531/131; C12Q 2537/149; C12Q 1/24; C12Q 1/68; C12Q 1/707; C12Q 1/6869; C12Q 2565/607; C12Q 2531/113; C12Q 1/6804; C12Q 1/706; C12Q 1/6874; C12Q 2500/00; C12Q 2560/00; C12Q 2600/16; C12Q 2600/166; G01N 33/6848; G01N 2333/36; G01N 33/56983; G01N 2333/08; G01N 2333/183; G01N 2333/185; G01N 2333/186; G01N 2400/00; G01N 21/3577; G01N 33/54366; G01N 33/577; G01N 33/582; G01N 33/6845; G01N 33/6851; G01N 1/4077; G01N 33/68; G01N 33/6842; G01N 33/6854; G01N 2458/15; G01N 2560/00; G01N 2800/52; G01N 30/02; G01N 2800/50; G01N 30/24; G01N 33/58; G01N 33/6857; G01N 2030/885; G01N 2030/8886; G01N 2035/1058; G01N 27/00; G01N 27/622; G01N 35/0098; G01N 35/085; H01L 21/28; G16H 50/20; G16H 10/40; G16H 30/00; G16H 80/00; G06F 3/14; H01J 49/0031; H01J 49/0036; H01J 49/00; H01J 49/0004

See application file for complete search history.

(56) References Cited

U.S. PATENT DOCUMENTS 8,476,009 B2 * 7/2013 Li ........................... A61P 31/12
435/5

OTHER PUBLICATIONS

Leroy et al. Lacent Jun. 24, 2000; 355(9222):2210-5. doi: 10.1016/s0140-6736(00)02405-3.*
2D Gel Electrophoresis Buffers and Reagents by Thermal Fisher Scientific printed by Sep. 8, 2020.*
Fausther-Bovendo et al. (Scientific Reports (2017), 7, 42147 CODEN: SRCEC3; ISSN: 2045-2322.*
Abcam published since 1998 till 2020. pp. 1-7.*
Pleet et al. J Infect Dis. Dec. 15, 2018; 218(Suppl 5): S365-S387. Published online Aug. 30, 2018.*
Fernando Cobo The Open Viology Journal 2013, vol. 7, pp. 84-90.*
David J. Harvey , Expert Review of proteomics , published by 2018, vol. 15, issue 5, pp. 391-412.*
Guidance for Collection, transport and Submitting of Specimens for Ebola virus Texting that Published by May 15, 2018.*
M. Jana Broadhurst, et al., "Diagnosis of Ebola Virus Disease: Past, Present, and Future," Clinical Microbiology Reviews, vol. 29, No. 4, Oct. 2016, pp. 773-793.
Mark Ratner, "Scripps boosts research coffers by selling reagents to Sigma-Aldrich," Nature Biotechnology, vol. 31, No. 10, Oct. 2013, pp. 862-864.
Neelja Singhal, et al., "MALDI-TOF mass spectrometry: an emerging technology for microbial identification and diagnosis," Frontiers in Microbiology, vol. 6, Article 791, Aug. 2015, pp. 1-16.
Shuo Su, et al., "Diagnostic strategies for Ebola virus detection," The Lancet, vol. 16, Mar. 2016, pp. 294-295.

* cited by examiner

*Primary Examiner* — Bao Q Li
(74) *Attorney, Agent, or Firm* — Noah J. Hayward (57) ABSTRACT

A method for a pre-symptomatic diagnosis of a viral illness in a subject is provided. The method may include obtaining a biological sample that includes at least one peripheral blood mononuclear cell from a subject prior to the subject experiencing any symptoms associated with the viral illness. The method may further include extracting proteins from the biological sample. The method may also include analyzing the extracted proteins, via mass spectrometry, for the presence of a predefined viral protein biomarker associated with the viral illness. If the predefined viral protein biomarker is present, the subject is diagnosed with the viral illness prior to experiencing the symptoms associated with the viral illness.

16 Claims, 6 Drawing Sheets

| TMT Experiment | Method of Infection | | Sex | | Days post-infection (number of samples) | | | |
|---|---|---|---|---|---|---|---|---|
| | Aerosol | IM | Male | Female | 0 | 3 | 3 | 5 |
| 1 | 3 | - | 2 | 1 | 3 | 3 | 3 | 3 |
| 2 | 3 | - | - | 3 | 3 | 3 | 3 | 3 |
| 3 | - | 3 | 2 | 1 | 3 | 3 | 3 | 3 |

FIG. 4

| TMT Experiment | Number of Proteins | | |
| --- | --- | --- | --- |
| | Identified | Quantified | PCA Analysis |
| 1 | 6425 | 6425 | 5823 |
| 2 | 6820 | 6228 | 5997 |
| 3 | 6781 | 6260 | 6234 |

PRE-SYMPTOMATIC DIAGNOSIS OF A VIRAL ILLNESS

STATEMENT OF GOVERNMENTAL INTEREST

This invention was made with Government support under contract number 2012-12-50800010 awarded by the Intelligence Advanced Research Projects Activity (IARPA). The Government has certain rights in the invention.

TECHNICAL FIELD

Example embodiments generally relate to a pre-symptomatic diagnosis of a viral illness.

BACKGROUND

Ebola Virus Disease (EVD) is a disease that is caused by a virus of the Filoviridae family. Currently, there are four identified EVD species that are known to cause disease in humans: Zaire ebolavirus, Sudan ebolavirus, Tai Forest ebolavirus, and Bundibugyo ebolavirus. Health care professionals deployed to an area experiencing an outbreak of EVD are required to have a 21-day quarantine period before leaving the area to ensure they are not infected by EVD or are contagious.

In this respect, the incubation period of EVD in a person may vary from anywhere to 2 to 21 days, with the first symptoms commonly being fever, fatigue, muscle pain, headache, and sore throat. The first symptoms are then generally followed by vomiting, diarrhea, rash, impaired kidney and liver function, and in some cases, both internal and external bleeding. Based on the initial symptoms, EVD can be difficult to clinically distinguish from other infectious diseases such as malaria, typhoid fever, and meningitis. Currently, the average EVD diagnosis is not made until five days after the onset of symptoms. The longer EVD is left untreated in a person the costlier the treatment becomes and the greater likelihood EVD may prove fatal and increase the likelihood of Ebola virus (EBOV) transmission during epidemics.

BRIEF SUMMARY

Accordingly, in order to enable the pre-symptomatic diagnosis of viral illnesses, example embodiments provide methods and diagnostic kits that are configured to detect a viral illness in a subject after suspected exposure to the viral illness rather than upon the onset of symptoms associated with the viral illness. Accordingly, by enabling the pre-symptomatic diagnosis of viral illnesses, long quarantine periods will not be required, the treatment associated with the viral illness may be less costly and intensive, and there is a higher likelihood of recovery in the subject before the individual is likely to transmit the disease.

In one example embodiment, a method for a pre-symptomatic diagnosis of a viral illness in a subject is provided. The method may include obtaining a biological sample that includes at least one peripheral blood mononuclear cell from a subject prior to the subject experiencing any symptoms associated with the viral illness. The method may further include extracting proteins from the biological sample. The method may also include analyzing the extracted proteins, via mass spectrometry, for the presence of a predefined viral protein biomarker associated with the viral illness. If the predefined viral protein biomarker is present, the subject is diagnosed with the viral illness prior to experiencing the symptoms associated with the viral illness.

In a further example embodiment, a method for a pre-symptomatic diagnosis of a viral illness in a subject is provided. The method may include obtaining a biological sample that includes at least one peripheral blood mononuclear cell from a subject prior to the subject experiencing any symptoms associated with the viral illness. The method may also include stimulating the biological sample. The stimulation of the biological sample may include adding a predetermined amount of reagent to the biological sample to produce a mixture, and the reagent may be configured to have a binding reaction in a presence of a predefined viral protein biomarker associated with the viral illness. The method may additionally include analyzing the mixture to determine if the reagent had the binding reaction. If the binding reaction is detected, the subject may be diagnosed with the viral illness prior to the subject experiencing symptoms of the viral illness In an even further example embodiment, a diagnostic kit for a pre-symptomatic diagnosis of a viral illness in a subject is provided. The diagnostic kit may include a well configured to hold a biological sample from the subject. The diagnostic kit may also include a predetermined amount of reagent. The reagent may be configured to have a binding reaction that is determinative of a presence of a predefined viral protein biomarker associated with the viral illness in the biological sample.

BRIEF DESCRIPTION OF THE DRAWING(S)

Having thus described some example embodiments of the invention in general terms, reference will now be made to the accompanying drawings, which are not necessarily drawn to scale, and wherein:

DETAILED DESCRIPTION

Some example embodiments now will be described more fully hereinafter with reference to the accompanying drawings, in which some, but not all example embodiments are shown. Indeed, the examples described and pictured herein should not be construed as being limiting as to the scope, applicability or configuration of the present disclosure. Rather, these example embodiments are provided so that this disclosure will satisfy applicable legal requirements. Like reference numerals refer to like elements throughout. Furthermore, as used herein, the term "or" is to be interpreted as a logical operator that results in true whenever one or more of its operands are true.

The term "peripheral blood mononuclear cells (PBMC)" may include any blood cell having a round nucleus. Such cells are known to play a role in the immune response. PBMC may include for instance lymphocytes such as T-cells, B-lymphocytes and NK cells, monocytes, and macrophages. The PBMC may correspond to a B-lymphocyte. The term "B lymphocyte" may refer to B-lymphocytes.

The term "mass spectrometry" refers to a method of using a mass spectrometer, such as a gas phase ion spectrometer, to measure a parameter that can be translated into mass-to-charge ratios of gas phase ions.

The term "antibody" may refer to a polypeptide or group of polypeptides, which are comprised of at least one binding domain configured to specially bind with a predetermined biomarker or set of biomarkers. Antibodies include recombinant proteins comprising the binding domains, as wells as fragments, including Fab, Fab', F(ab)2, and F(ab)2 fragments. In some embodiments, when the epitope is an amino acid sequence, an epitope may include as few as 3 amino acids in a spatial conformation which is unique to the epitope. Generally, an epitope may include at least 6 amino acids, and in some cases, at least 8-10 amino acids. Many antibodies are available commercially and in addition, antibodies also may be produced by methods well known in the art, e.g., by immunizing animals with the virus.

The term "biomarker" refers to a viral protein which is present or differentially present in a sample taken from a subject having a virus compared to a comparable sample taken from control subjects (e.g., a person with a negative diagnosis or a normal or healthy subject that has not been exposed to the virus or has not been in an area experiencing viral outbreaks, etc.).

The term "host protein" refers to any proteins derived from cells of a subject or individual from which a biological sample was obtained.

The term "viral protein" refers to any proteins derived from a virus, disease, or viral source.

The term "sample," "patient sample," "biological sample," and the like, may encompass a variety of sample types obtained from a patient, individual, or subject and may be used to diagnosis a viral illness. The sample may be obtained from a healthy subject, a diseased patient, or a patient exposed to a virus.

The term "control sample" may mean any control or standard familiar to one of ordinary skill in the art useful for comparison purposes. For example, the control sample may be obtained from a person not infected with the virus being tested.

EVD is a hemorrhagic disease caused by EBOV that usually results in fatality if untreated at the earliest signs of clinical symptoms. EBOV is a virus that contains a single-stranded RNA genome that encodes seven viral proteins: nucleoprotein (NP), glycoprotein (sGP), L-polymerase (L), viral protein (VP) 24, VP30, VP35, and VP40. L is an RNA-dependent RNA polymerase (RdRp) that forms an RdRp complex with VP30. VP30 is responsible for viral genome transcription and replication. VP24 and VP35 inhibit interferon (IFN) signaling and facilitate evasion of the host immune response. NP encapsidates the viral genome into the nucleocapsid, while VP40 drives viral assembly and budding. sGP is on the surface of the virion and is essential for binding to target cells and subsequently mediating membrane fusion and the release of the viral genome.

EBOV is configured to invade almost all human cells using different attachment mechanisms for each cell type. In some cases, EBOV enters target human cells by using different uptake mechanisms including lipid raft, receptor-mediated endocytosis, and micropinocytosis. An individual or subject infected with EBOV may mount a strong inflammatory response. The inflammatory process is then followed by a T-cell response leading to the generation of EBOV-specific IgG1 and IgG3 subclass responses and to marked and sustained activation of cytotoxic cells involved in the elimination of infected cells from peripheral circulation. In other words, EBOV may infect the cells of a subject and the infected cells may display signals of an infection on the surface of the cell to activate T-lymphocytes—the white blood cells that are helpful in destroying other infected cells before the virus replicates further.

EVD is not typically diagnosed until 2-5 days after the onset of symptoms of the disease. Accurate and early detection of EVD prior to the onset of symptoms may result in a more successful and less costly and intensive treatment plan for the subject and thus less likelihood of fatality associated with the disease. Different types of diagnostic testing are currently available to detect EVD, such as enzyme-linked immunosorbent assay ("ELISA") and polymerase chain reaction ("PCR"). However, these known diagnostic tests are generally only capable of detecting the presence of virus specific markers after the onset of symptoms. Moreover, these types of tests typically have low sensitivity and may produce false negatives or false positives.

However, as further discussed herein, a plurality of EBOV viral proteins may be detectable in a subject prior to onset of symptoms of the disease and serve as biomarkers for the pre-symptomatic detection of the viral illness in the subject. In this regard, rather than have to undertake complicated calculations to determine changes in a subject's host proteins, the detection of the presence (e.g., a detected level of more than 0.0) of viral proteins associated with a particular virus may enable the subject to be diagnosed with the virus even before symptoms are experienced by the subject. In other words, viral proteins associated with a virus may be detectable in a biological sample of a subject even before the subject experiences symptoms associated with the virus. For example, the presence of any of the viral protein associated with EBOV or combination thereof [e.g., any single one or combination of 1) NP (GenBank Protein Accession No: AAM76031.1), 2) VP40 (GenBank Protein Accession No: AAM76033.1), 3) VP30 (GenBank Protein Accession No: ADM72999.1), 4) VP35 (GenBank Protein Accession No: AAM76032.1), or 5) sGP (GenBank Protein Accession No: AAM76034.1)] in a subject may serve as a biomarker and is detectable in a biological sample of a subject before the subject begins experiencing symptoms of the disease. In particular, these EBOV biomarkers are present in a subject before the subject exhibits any clinical symptoms or viremic indications. For example, EVD, through the detection of associated viral proteins, may be diagnosable prior to the subject experiencing any of the following symptoms: fever, fatigue, muscle pain, headache, sore throat, vomiting, diarrhea, rash, impaired kidney or liver function, or internal or external bleeding.

By the identification of these viral protein biomarkers in a biological sample of the subject, EVD or any other virus may be easily tested for and accurately diagnosed at an early stage to not only improve the outcome of medical interventions before the subject experiences symptoms, but will significantly contribute to controlling the spread of the disease during an outbreak. In other words, the detection of a mere presence of a viral protein in a subject's biological sample allows for easy detection of a virus without having to perform complicated calculations to determine if there have been any changes to the subject's host proteins the like.

Furthermore, a pre-symptomatic diagnosis of EVD would obviate the need for any mandatory 21-day quarantine period of personnel who are deployed to potential outbreak zones, as the methods and diagnostic kits provided herein may render an accurate diagnosis within at least 2-5 days from exposure to EBOV. Accordingly, certain EBOV proteins (e.g., NP, VP40, VP30, VP 35, or sGP) may serve as biomarkers of EVD and may be tested for and detected prior to the subject experiencing symptoms associated with the virus.

Accordingly, methods and diagnostic kits for the pre-symptomatic diagnosis of a viral illness (e.g., EVD) are provided herein. It should be understood that although EVD is the viral illness frequently referenced throughout, the methods and diagnostic kits described herein could be applicable to a wide variety of viral illnesses.

Figure 1:
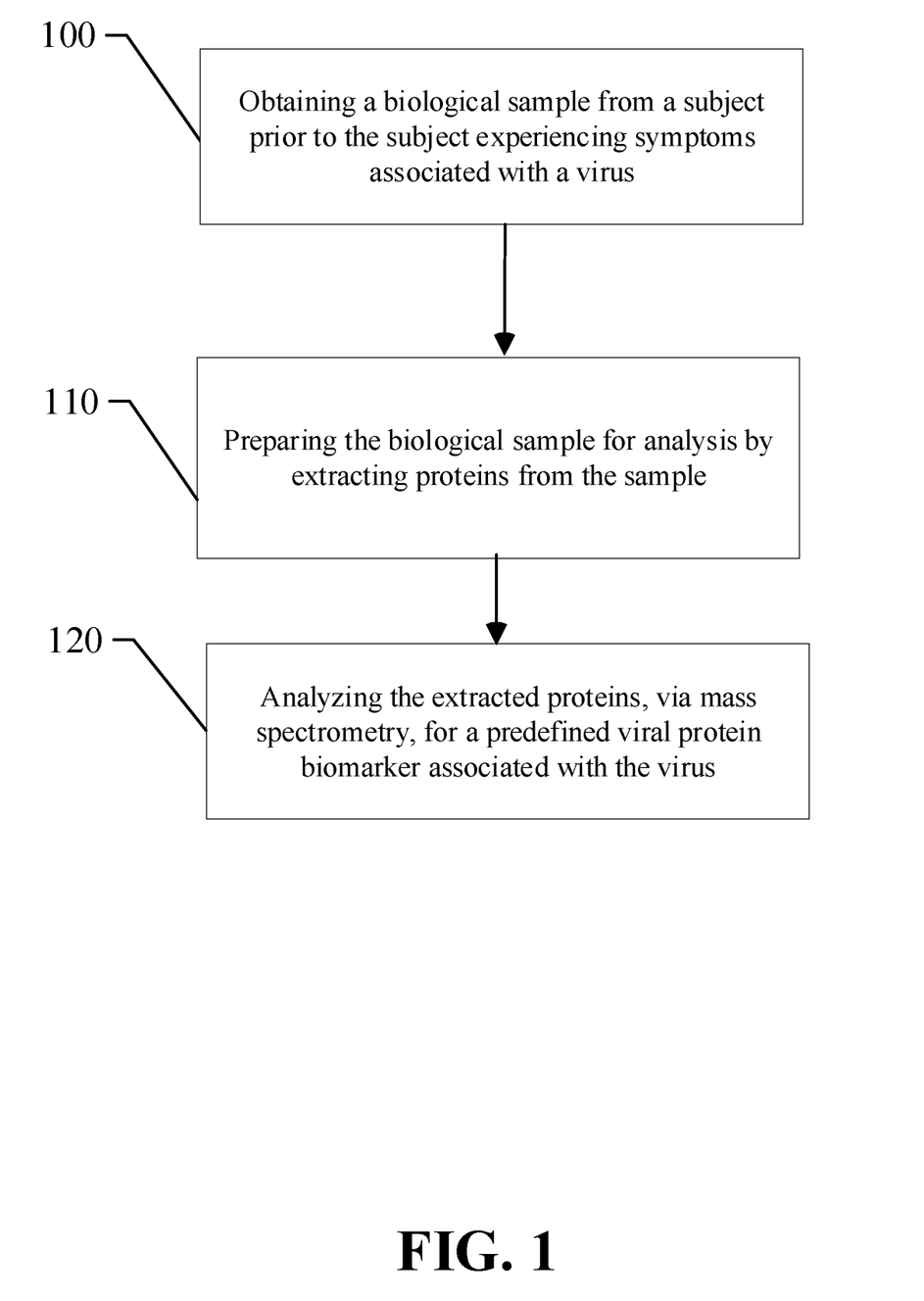
FIG. 1 illustrates a method for a pre-symptomatic diagnosis of a viral illness according to an example embodiment.

FIG. 1 illustrates a method for the pre-symptomatic diagnosis of the viral illness according to an example embodiment. As shown in FIG. 1, the method may include, at step 100, obtaining a biological sample from a subject. The biological sample may be taken prior to the subject experiencing symptoms associated with the virus. It should be understood, however, that the methods and kits used herein may also be used after the subject begins experiencing symptoms in order to confirm if the subject is infected with the virus. In some cases, the subject may have been in an area experiencing a viral outbreak, or the subject may suspect they have been exposed to the virus. Furthermore, the biological sample may be obtained by a health care worker or professional by drawing blood from the subject. However, in some cases, the health care professional may obtain the biological sample by collecting tissue from the subject (e.g., lymphoid tissue) or the like.

It should be understood that the subject may be a human subject. In some cases, however, the subject may be a non-human primate such as a monkey, ape, or the like. Accordingly, the method may be used for medical, veterinary, or development purposes. Furthermore, a time range in which the biological sample may be obtained by the health care profession may vary based on the route of exposure, type of animal being tested, number of EBOV particles, etc. For example, the time range in which the biological sample may be obtained may vary from 0 hours to 21 days within suspected exposure to the virus, or in some cases later than 21 days. For example, the time range in which the biological sample may be obtained may be at most about 21, 20, 19, 18, 17, 16, 15, 14, 13, 12, 11, 10, 9, 8, 7, 6, or 5 days or at least about any of 5 hours, 6 hours, 7 hours, 8 hours, 9 hours, 10 hours, 11 hours, 12 hours, 15 hours, 18 hours, or 1, 2, 3, or 4 days. In accordance with some example embodiments, a sample from a non-human primate having 1,000 plaque forming units(PFU)/µ of EBOV demonstrates that the non-human primate typically develops symptoms at day five. However, it should be understood that at low doses or in other routes of exposure, the presentation of symptoms may be delayed in the subject.

In accordance with example embodiments, the biological sample may include at least one peripheral blood mononuclear cell (PBMC) from a subject, and in some cases, a plurality of PBMCs. Furthermore, the biological sample collected may include a plurality of proteins. After obtaining the biological sample, the biological sample may be prepared for analysis to determine if the subject has been exposed to a virus (e.g., EBOV) at step 110.

The preparation of the biological sample may include isolating or separating the proteins from the overall biological sample to aid in the detection of certain viral proteins via mass spectrometry. Proteins are generally embedded in biological material or are associated with other proteins, biological molecules, or other matrix materials. For example, proteins may be part of multi-protein complexes or integrated into plasma membranes. By isolating or separating the proteins from the overall biological sample, the presence of certain viral proteins associated with the virus being tested for may be detectable via mass spectrometry. The isolation of the proteins from the biological sample may be accomplished via any methods known to those skilled in the art. For example, in some cases, the isolation of the proteins from the overall biological sample may be done by filter-aided sample preparation (FASP), in which the proteins of interest (e.g., VP40, VP30, VP35, NP, and/or sGP) may be extracted from the biological sample. As further described below, the biological sample may be subject to at least one lysis buffer, reduction and alkylation, and digestion to extract proteins of interest from the sample.

In this regard, the first step in isolating the proteins from the biological sample may include lysis of the biological sample. In some embodiments, lysis of the biological sample may include adding a predetermined amount of a lysis buffer to the biological sample. In some cases, the lysis buffer may be a predetermined amount of Trizol™ reagent (Invitrogen) (e.g., about 0.4 mL of Trizol™ Reagent per $1 \times 10^5$-$10^7$ cells). In other example embodiments, the lysis of the biological sample may be achieved by the addition of a predetermined amount of radio immunoprecipitation assay (RIPA) lysis buffer to the biological sample. In this regard, the RIPA lysis buffer may include, for example, 50 mM Tris hydrochloride (HC1) pH 8, 150 mM sodium chloride (NaCl), 1% NP-40, 0.5% sodium deoxycholate, and 0.1% sodium dodecyl sulfate (SDS).

In even further example embodiments, the lysis of the biological sample may be achieved by the addition of a predetermined amount of an urea-based lysis buffer. The urea-based buffer may include, for example, TRIS base 40 mM, Urea 7 M, Thiourea 2 M, NP-40 or CHAPS 4%, dithiothreitol (DTT) 10 mM. Furthermore, the mixture of the lysis buffer and biological sample may be incubated at a predefined temperature (e.g., about 37° C.) to ensure complete cell lysis, and then the mixture may be subjected to centrifugation to separate the cells from the mixture.

In accordance with other example embodiments, the lysis of the biological sample may be achieved by mechanical disruption such as the use of glass beads. It should be understood that the lysis of the biological sample may include using only one of the methods described above or a combination thereof. Regardless of the combination of lysis steps employed, the lysis of the biological sample may result in a protein fraction The protein fraction may then be reduced and alkylated and then digested for proteomics analysis on mass spectrometry. In this regard, it may be desirable to cleave the biomolecules or proteins in the protein fraction into smaller fragments using cleaving reagents, such as proteases. In some cases, the cleaving reagent used may be or include a predetermined amount trypsin (e.g., about a 1:20 ratio of trypsin to total protein). The digestion of proteins or biomolecules into smaller fragments may be useful in determining or improving the resolution of certain viral protein biomarkers. Furthermore, smaller fragments may be more easily resolved by mass spectrometry.

In accordance with some example embodiments, once the biomolecules of the protein fraction are fragmented into proteins or peptides, for example, the step of preparing the biological sample may also include labeling the peptides. In this regard, a tag may be attached to the peptide or protein in order to more easily identify or classify the peptide during testing of the biological sample. In this regard, the peptides or proteins may be labeled by any means know in the art. For example, tandem mass tags (TMT) or the like may be used to label the proteins or peptides.

As shown in FIG. 1, after the biological sample is prepared, the extracted proteins may be analyzed at step 120. The analysis of the extracted proteins may include analyzing the proteins using mass spectrometry that enables accurate protein/peptide identification. The mass spectrometry performed may be any type of mass spectrometry known in the art that allows for the detection of certain predefined viral protein biomarkers associated with the virus being tested for, in which the mass spectrum plots the different mass-to-charge ratios (m/z) against the protein abundances (e.g., occurrence of a certain ion divided by the occurrence of the most plentiful ion) within the sample. For example, when EVD is being tested for, the presence (e.g., any level above 0.0) of any of the EBOV viral proteins (i.e., NP, sGP, L, VP24, VP30, VP35, and VP40) in the biological sample may indicate that the subject has been infected with EVD thereby resulting in a positive diagnosis of the virus. This is contrast to a control sample that would have 0.0 level of any of NP, sGP, L, VP24, VP30, VP35, or VP40 as the subject from which the control sample was taken has not been exposed to the virus and therefore would have no viral proteins associated with the virus.

In this respect, a peptide fragment of VP35 and VP30 may be detectable in the digested samples by mass spectrometry as a MS/MS spectral even before symptoms are experienced by the subject. The pre-symptomatic presence (e.g., above a 0.0 level) of VP35 and/or VP30 in the mass spectrometry results may indicate the infection of EVD in the subject, even though the subject has yet to experience any symptoms associated with the virus. In this regard, just the presence of one or more viral proteins in the mass spectrometry results may result in a positive diagnosis of the virus associated with the viral proteins detected.

Furthermore, a calculated abundance (e.g., ratio of viral proteins to overall proteins in sample) of the viral protein in the tested biological sample may be correlated to how many days post-exposure the subject is. For example, the abundance of VP35 may increase in the sample the more days the subject is infected with the virus. In this regard, the abundance of VP35 in a PBMC sample may be at about 1.5-fold at day 3 and increase to about 3-fold at day 5 post-exposure. Accordingly, the presence and abundance change of VP35 may serve as an indicator of EVD and may enable the extrapolation of the time the subject could become viremic without intervention. Therefore, the abundance of VP35 detected in the sample may serve as guide for forming a treatment plan for the subject.

Furthermore, a peptide fragment derived from VP40 may be detectable by mass spectrometry before symptoms are experienced by the subject. The presence of VP40 in the mass spectrometry results may indicate the infection of EVD in the subject, even though the subject has yet to experience any symptoms associated with the virus. However, in some cases, the presence and abundance change of VP40 may serve as an indicator of EVD and may enable the extrapolation of the time the subject could become viremic without intervention.

In this regard, a calculated abundance of VP40 in the tested biological sample may be correlated to how many days post-exposure the subject is. For example, the abundance of VP40 may increase in the sample the more days the subject is infected with the virus. In this regard, the abundance of VP40 in the biological sample may be above a 0.0 level baseline at day 1 and increase to about 3-fold at day 5 post-exposure. Accordingly, the abundance of VP40 may serve as an indicator of how long the subject has until symptoms may begin and therefore may serve as guide for forming a treatment plan for the subject.

Additionally, a peptide fragment derived from sGP may be detectable by mass spectrometry even before symptoms are experienced by the subject. The presence of sGP in the mass spectrometry results may indicate the infection of EVD in the subject, even though the subject has yet to experience any symptoms associated with the virus. Furthermore, in some cases, a calculated abundance of sGP in the tested biological sample may be correlated to how many days post-infection the subject is.

For example, a calculated abundance of sGP in the tested biological sample may be correlated to how many days post-exposure the subject is. The abundance of sGP may increase in the sample the more days the subject is infected with the virus. In this regard, the abundance of sGP in the biological sample may be above a 0.0 baseline level at day 3 and increase about 2.5-fold at day 5 post-exposure. Accordingly, the abundance of sGP may serve as an indicator of how long the subject has until symptoms may begin and therefore may serve as guide for forming a treatment plan for the subject.

As mentioned above, the presence of any of NP, sGP, L, VP24, VP30, VP35, or VP40 or combination thereof in the mass spectrometry performed before the subject begins experiencing symptoms may indicate that the subject has been infected with EBOV. However, in accordance with other example embodiments, a plurality of the predefined biomarkers may need to be present before a positive diagnosis of the virus may be made. In this regard, the presence of two or more from the combination of NP, sGP, L, VP24, VP30, VP35, or VP40 may indicate that the subject is infected with EVD. For example, in the case of EBOV, the presence of both VP35 and VP30 in the biological sample may indicate that the subject has been infected with EBOV. However, in even further example embodiments, the presence of three or more from the combination of NP, sGP, L, VP24, VP30, VP35, or VP40 may indicate that the subject is infected with EBOV. For example, the presence of NP, sGP, and VP 40 may indicate the subject has been infected with EBOV. Accordingly, mass spectrometry tests performed on a biological sample of a subject may aid in diagnosing a subject with a viral illness, such as EVD, before the subject beings experiencing symptoms thereby enabling quick and efficient treatment of the virus to prevent spread of the virus and improve the prognosis.

In certain embodiments, when the presence of a viral protein (e.g., any of NP, sGP, L, VP24, VP30, VP35, or VP40) is detected in a biological sample, the subject is diagnosed with the virus or disease associated with the viral protein. When the diagnosis is made, the method may include an additional step of providing a recommendation for treatment of the virus or disease. For example, if the subject is diagnosed with EVD based on the presence of a EBOV biomarker being detected in the subject's biological sample, a healthcare professional may make a treatment recommendation to ensure quick and efficient treatment of the subject in order to increase the likelihood of recovery in the subject and reduce the transmission of the virus or disease.

Figure 2:
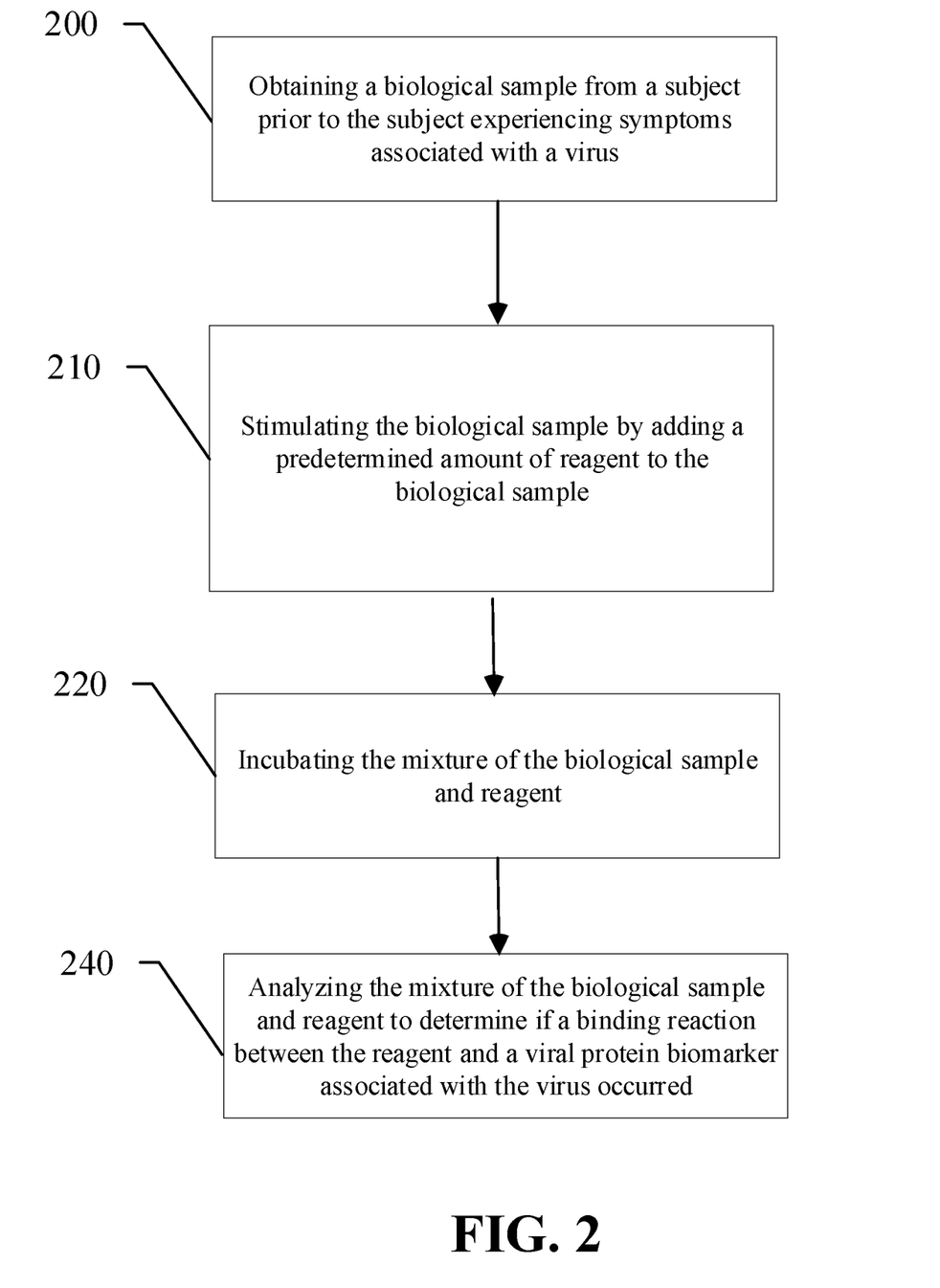
FIG. 2 illustrates a method for a pre-symptomatic diagnosis of a viral illness according to a further example embodiment.

FIG. 2 illustrates a further method for the pre-symptomatic diagnosis of the viral illness according to an example embodiment. The method, further detailed below, may utilize an immunoassay, such as an enzyme-linked immunospot ("ELISpot") assay, to detect the presence of virus biomarkers, such as EBOV biomarkers, in a biological sample of the subject before the onset of symptoms associated with the virus. In some cases, this method may be used when a health professional is working in an outbreak zone, for example, and has no access to mass spectrometry technology.

As shown in FIG. 2, the method may include, at step 200, a health care professional or clinician obtaining a biological sample from a subject. In some cases, the subject may suspect that they may have been exposed to the virus. Furthermore, the biological sample may be obtained by the health care professional by drawing blood from the subject. It should be understood that the subject may be a human subject. In some cases, however, the subject may be a non-human primate such as a monkey, ape, or the like. Accordingly, this method may also be used for medical, veterinary, or development purposes. Furthermore, a time range in which the biological sample may be obtained by the health care profession may vary based on the route of exposure, type of animal being tested, number of EBOV particles, etc. For example, the time range in which the biological sample may be obtained may vary from 0 hours to 21 days within suspected exposure to the virus, or in some cases later than 21 days. For example, the time range in which the biological sample may be obtained may be at most about 21, 20, 19, 18, 17, 16, 15, 14, 13, 12, 11, 10, 9, 8, 7, 6, or 5 days or at least about any of 5 hours, 6 hours, 7 hours, 8 hours, 9 hours, 10 hours, 11 hours, 12 hours, 15 hours, 18 hours, or 1, 2, 3, or 4 days. In accordance with some example embodiments, a sample from a non-human primate having 1,000 PFU/μ of EBOV demonstrates that the non-human primate may develop symptoms at day five. Accordingly, the sample may be obtained prior to day five. It should be understood that at low doses or in other routes of exposure the presentation of symptoms may be delayed in the subject. In accordance with example embodiments, the biological sample may include at least one PBMC from a subject.

In accordance with some example embodiments, after obtaining the biological sample, the biological sample may be fractioned or at least one PBMC may be isolated or separated from the overall biological sample. The isolation of the at least one PBMC may be done by any method known to one skilled in the art. For example, in some cases, the isolation of the at least one PBMC from the overall biological sample may be done by density gradient centrifugation.

As further shown in step 210 in FIG. 2, the biological sample, for example the entire sample, a fractioned portion, or the least one PBMC, may then be stimulated or activated. The stimulation of the biological sample may include, for example, adding a predetermined amount of reagent to the biological sample. The reagent may be configured to bind to a predefined biomarker or a plurality of predefined biomarkers associated with the virus being tested. In this regard, the reagent may be an antibody having specific binding properties to isolate, target, or quantify a predefined biomarker. In this regard, the antibody may be configured to have a binding reaction that is determinative of the presence of the predefined biomarker in the biological sample having a heterogeneous population of proteins and other biologics. In other words, the antibody may be configured to bind to a particular biomarker or protein and to not substantially bind in a significant amount to other proteins present in the sample. Accordingly, the antibody being used may tailored to have a specific binding affinity to a predetermined viral protein or biomarker to enable the diagnosis of a virus associated with the biomarker before the subject begins exhibiting symptoms associated with the virus.

The step of adding the predetermined amount of reagent may include pre-coating a well configured to be used in the immunoassay with a predetermined amount of reagent. The amount of reagent used per well may be based on the specific biomarker or combination of biomarkers being tested. However, in some cases, the amount of reagent used may be in the range of 200 ng to 1 g. Once the well is pre-coated with the reagent, the biological sample or at least one PBMC may be added to the well.

In accordance with an example embodiment, the biological sample may be added to well in the form of an extract or lysate. In this regard, the biological sample may be initially subjected to a lysis buffer, as mentioned above, resulting in an extract or lysate. The extract or lysate may be a solution of cellular proteins resulting when cells are lysed or broken apart, such as by shearing cells. In some cases, the extract or lysate may be in a crude, partially purified, or purified form. A crude extract or lysate may be a solution formed when cells are lysed or broken apart with only minimal purification of the cell antigens away from remaining cell components. A partially purified extract or lysate may be solution in which proteins have been extracted or purified away from some of the remaining components of the cell. A purified extract or lysate may be a solution in which proteins have been completely or substantially separated from remaining components of the cell. Accordingly, in some embodiments, the biological sample used may be in a crude form when added to or mixed with the reagent. In further example embodiments, the biological sample used may be in a partially-pure form when added to or mixed with the reagent. In even further example embodiments, the biological sample used may be in a pure form when added to or mixed with the reagent. It should be understood that the extract or lysate may be purified by any method known to one skilled in the art. For example, the extract or lysate may be purified by the use of a detergent or a chaotropic agent to disrupt particles followed by differential extraction and separation of the polypeptides by ion exchange chromatography, affinity chromatography, sedimentation according to density, or gel electrophoresis.

After adding the biological sample to the reagent, the mixture of the reagent and the biological sample may then be incubated at step 220. In some cases, the mixture of the reagent and the biological sample may be incubated for a predetermined time under a predefined condition. In some cases, the predetermined time and the predefined condition of the incubation may be dependent on the length of time since the subject's suspected exposure to the viral illness. For example, the predefined time and condition used for incubation may be based on: i) subject's initial exposure date; ii) subject's duration or repeated contact with infectious individuals; iii) amount of infectious sample that the subject was exposed to (e.g., number of virus), route of exposure, etc. Furthermore, the mixture may be incubated with the addition of a detection reagent. The detection reagent may allow for easier detection of any binding reaction the reagent may have had with any viral protein biomarkers present in the sample. The detection reagent may be a label such as magnetic beads (e.g., DYNABEADS®), fluorescent dyes, radiolabels, enzymes (e.g., horse radish peroxide, alkaline phosphatase and others commonly used in an ELISA), or colorimetric labels such as colloidal gold or colored glass or plastic beads.

In some cases, the mixture may be incubated anywhere from 1-5 hours at room temperature. For example, if the subject suspects they were exposed recently to the viral illness, such as in the last 1-2 days, the incubation time period for the mixture may be longer, such as 3-5 hours. However, if the subject suspects they were exposed to the viral illness within the last 3-5 days or longer, the incubation time period for the mixture may only be 1-3 hours.

After the incubation period, the mixture of the biological sample and reagent may then be analyzed as shown in step 240. The analysis of the mixture includes determining if any binding reaction between the reagent and any present biomarkers have occurred. In the case of EVD, the reagent may be configured to bind to any of the viral proteins associated with EVD. Thus, if any EBOV viral proteins are present in the sample, then the binding reaction will be present. However, in some cases, the reagent may only be configured to bind with a single EBOV associated protein of protein fragment (e.g., VP35). In this case, if VP35 is present in the sample, the binding reaction will be present. In other words, the reagent may be configured to bind with multiple biomarkers indicative of a virus or only a single biomarker.

The detection of the binding reaction may include measuring the amount of, or presence of, an antibody-marker complex including, for example, detection of fluorescence, luminescence, chemiluminescence, absorbance, reflectance, transmittance, birefringence or refractive index (e.g., surface plasmon resonance, ellipsometry, a resonant mirror method, a grating coupler waveguide method or interferometry). Optical methods include microscopy (both confocal and non-confocal), imaging methods and non-imaging methods. Electrochemical methods include voltametry and amperometry methods. Radio frequency methods include multipolar resonance spectroscopy. Accordingly, immunoassays may also be used to determine presence or absence of a viral protein biomarker in the biological sample prior to viral symptoms being experienced by the subject.

Figure 3:
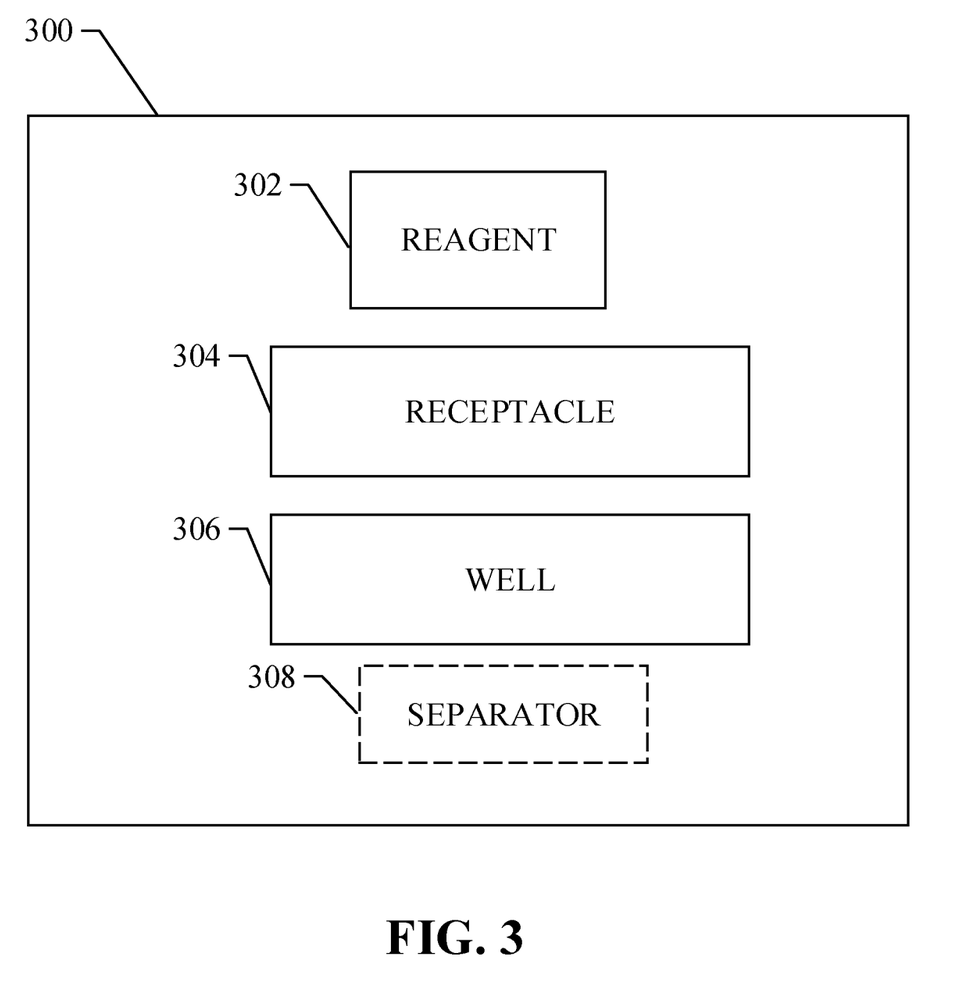
FIG. 3 illustrates a diagnostic kit according to an example embodiment.

In a further example embodiment, a diagnostic kit for practicing the above-disclosed immunoassay method may be provided. FIG. 3 illustrates the diagnostic kit for the pre-symptomatic diagnosis of a viral illness according to an example embodiment. In general, the diagnostic kit 300 may contain some or all of the components, reagents, supplies, or the like to practice the above-disclosed immunoassay method. Accordingly, the diagnostic kit 300 may refer to any intended article of manufacture (e.g., a package or a container) that includes a reagent and a set of particular instructions for practicing the method.

The kit may be used to measure any one or more of the biomarkers described herein, which biomarkers are present in biological samples of subject infected by the virus associated with the biomarker. Thus, the diagnostic kit 300 for the pre-symptomatic diagnosis of the viral infection may include at least one reagent 302 that is configured to bind a predefined biomarker or combination of biomarkers associated with the virus being tested. For example, when EVD is tested for, the reagent may be configured to bind a single one of or a combination of the EBOV viral proteins, including NP, sGP, L, VP24, VP30, VP35, or VP40. It should be understood that the kit 300 may include a plurality of reagents, where each reagent is configured to test for certain predefined biomarkers associated with the virus. In the case of testing for EVD, for example, a first capture reagent may be configured to bind to VP35 and VP30 and a second capture reagent may be configured to bind to sGP.

In further example embodiments, the diagnostic kit 300 may also include a receptacle 304 for collecting the biological sample from the subject, such as a syringe, tube, a blood collection tube, or the like. In further embodiments, the diagnostic kit may include a well 306 for conducting the immunoassay. In some cases, the well may be pre-coated with the reagent 302. Furthermore, when it is desired to separate the at least one PBMC from the biological sample, the diagnostic kit 300 may also include a separator 308 for separating the at least one PBMC from the other components of the biological sample of the subject. However, in other example embodiments, when it the biological sample may need to be fractioned before being tested, the kit 300 may include a fractionation solution or the like.

Example embodiments therefore represent a method and a diagnostic kit for the pre-symptomatic diagnosis of a viral illness. In this respect, the methods and kit discussed herein allow for the detection of the presence of viral protein biomarkers in a biological sample of the subject prior to the subject experiencing symptoms associated with the virus. By being able to easily detect viral proteins in a subject at such an early stage, the outcome of medical interventions and control of the spread of the disease is significantly improved.

The following example is provided to enable one of skilled in the art to practice the invention and is merely illustrative and in no way should be construed as being limiting. In this regard, the example should not be read as limiting the scope of the present disclosure.

In this experiment, commercial PBMCs were infected with EBOV and used to optimize and determine total protein recovery after RNA and DNA were extracted from about a half to one million cells that were treated with a chemical reagent for use in isolating biological material from organic tissue, specifically, aTRIZOL® lysis buffer. In this respect, protein extracts of TRIZOL®-treated, Ebola-infected PBMCs from a plurality of subjects were tested.

Six subjects were infected via aerosol and were tested at day 0 (prior to exposure), day 3 post-exposure, day 5 post-exposure, and at necrosis (NEC). Three subjects were infected via intramuscular (IM) and were tested at day 0, day 3 post-exposure, day 5 post-exposure, and day 7 post-exposure.

Figure 4:
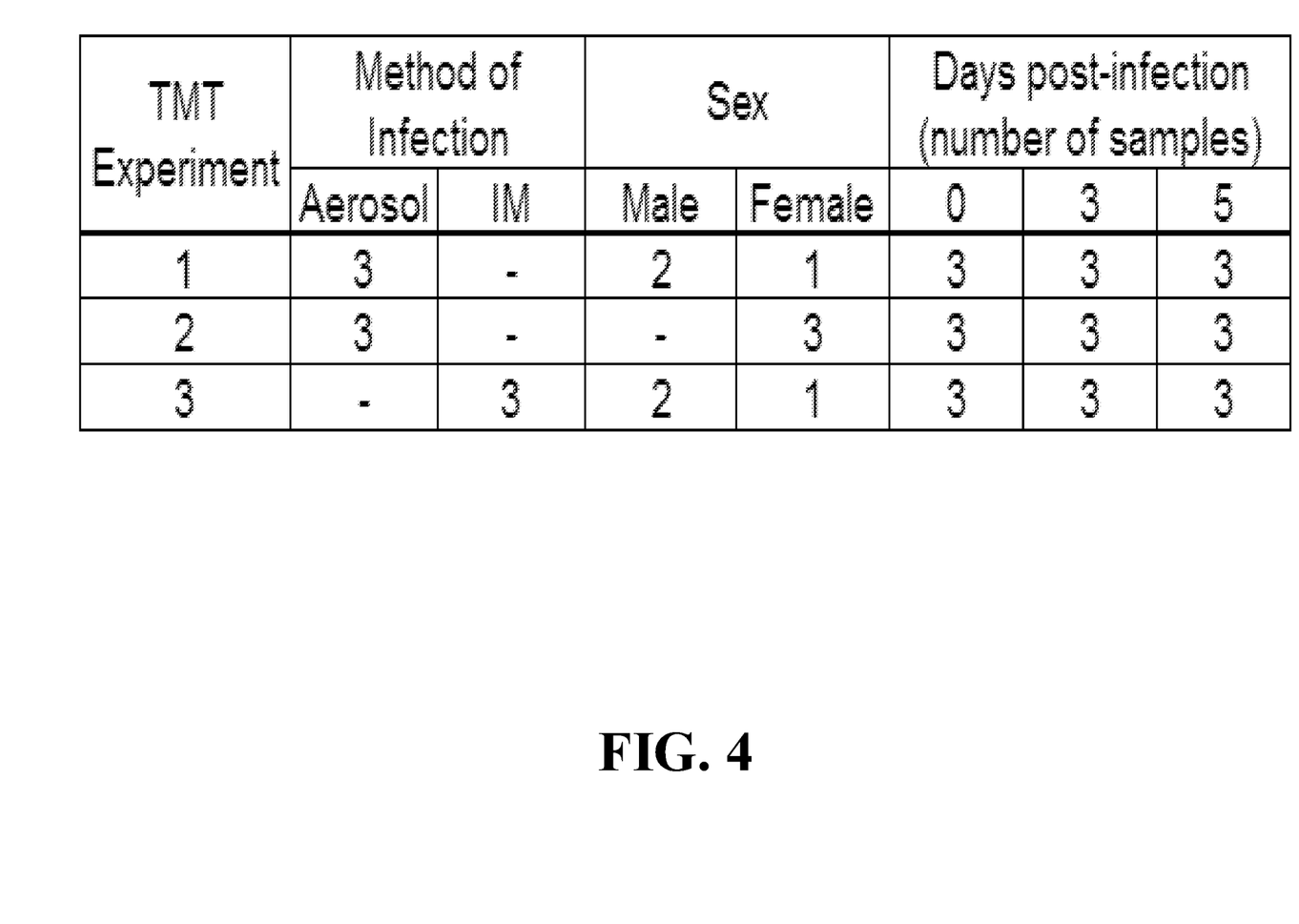
FIG. 4 illustrates a graphical representation of a summary of an experimental design for testing for viral proteins associated with a virus in a subject according to an example embodiment.

FIG. 4 illustrates a summary of an experimental design conducted. In this regard, the experimental design for comparing proteomic profiles of the subjects was as follows: a quantitative proteomic profile of the subjects using TMT isobaric mass tags were compared. The six aerosol-infected subjects were analyzed separately from the three subjects infected via IM. Samples were selected randomly per TMT experiment and time points to ensure randomized assignment of 10 channels within each TMT experiment. Three TMT quantitative proteomic analysis were performed on the nine PBMC protein extracts (6 aerosol and 3 IM infected individuals at 0, 3 and 5 days post infection). In addition, 6 NEC PBMC protein extracts from the aerosol infected subjects were also analyzed.

Figure 5:
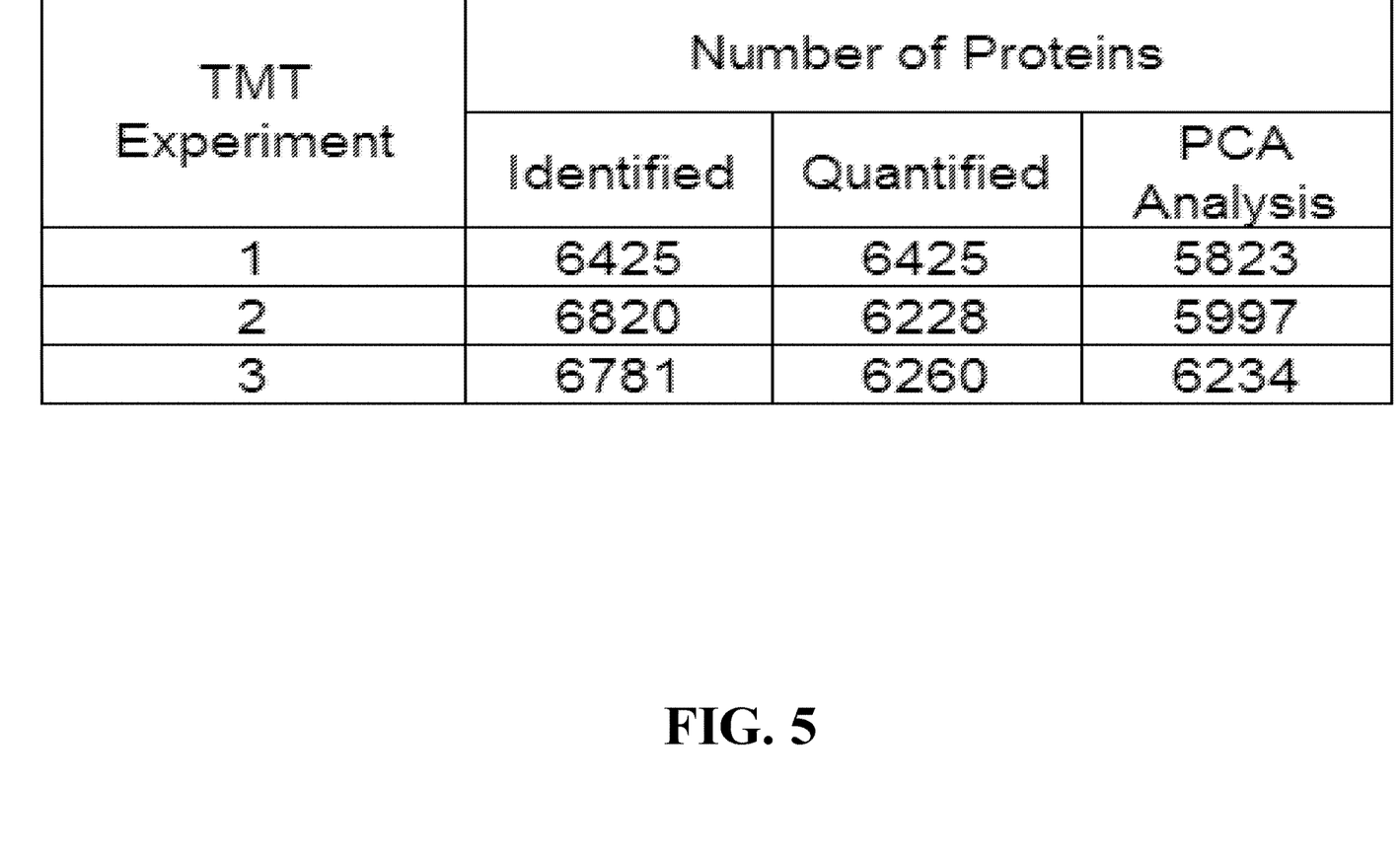
FIG. 5 illustrates a graphical representation of a summary of results of an experimental design for testing for viral proteins associated with a virus in a subject according to an example embodiment.

FIG. 5 illustrates a graphical representation of a summary of results of an experimental design testing for viral proteins in a subject. As shown in FIG. 5, multiple proteins were identified and quantified in each TMT experiment. In this respect, fractionation of the TMT labeled samples into 24 fractions was performed to identify and quantify thousands of proteins. Principal component analysis was also performed on the quantified proteins. The results confirmed that the commercial PBMCs protocol, such as buffer exchange, protein determination, protein digestion, were transferable to the TRIZOL®-treated, Ebola-infected PBMC protein extracts. Plasma proteins, mainly hemoglobin or albumin, were identified but were not the most abundant proteins and were found not to confound the TMT quantitative proteomic profiling experiments. About 500 proteins at a 5% false discovery rate (FDR) from a single 90 min LCMS/MS analysis were identified. In this regard, samples in TMT 3 (infected by IM) clustered significantly by time, indicating significant protein differences between 0, 3 and 5 post exposure time points. Samples in TMT 1 and TMT 2 (infected by aerosol) did not cluster by time.

Figure 6:
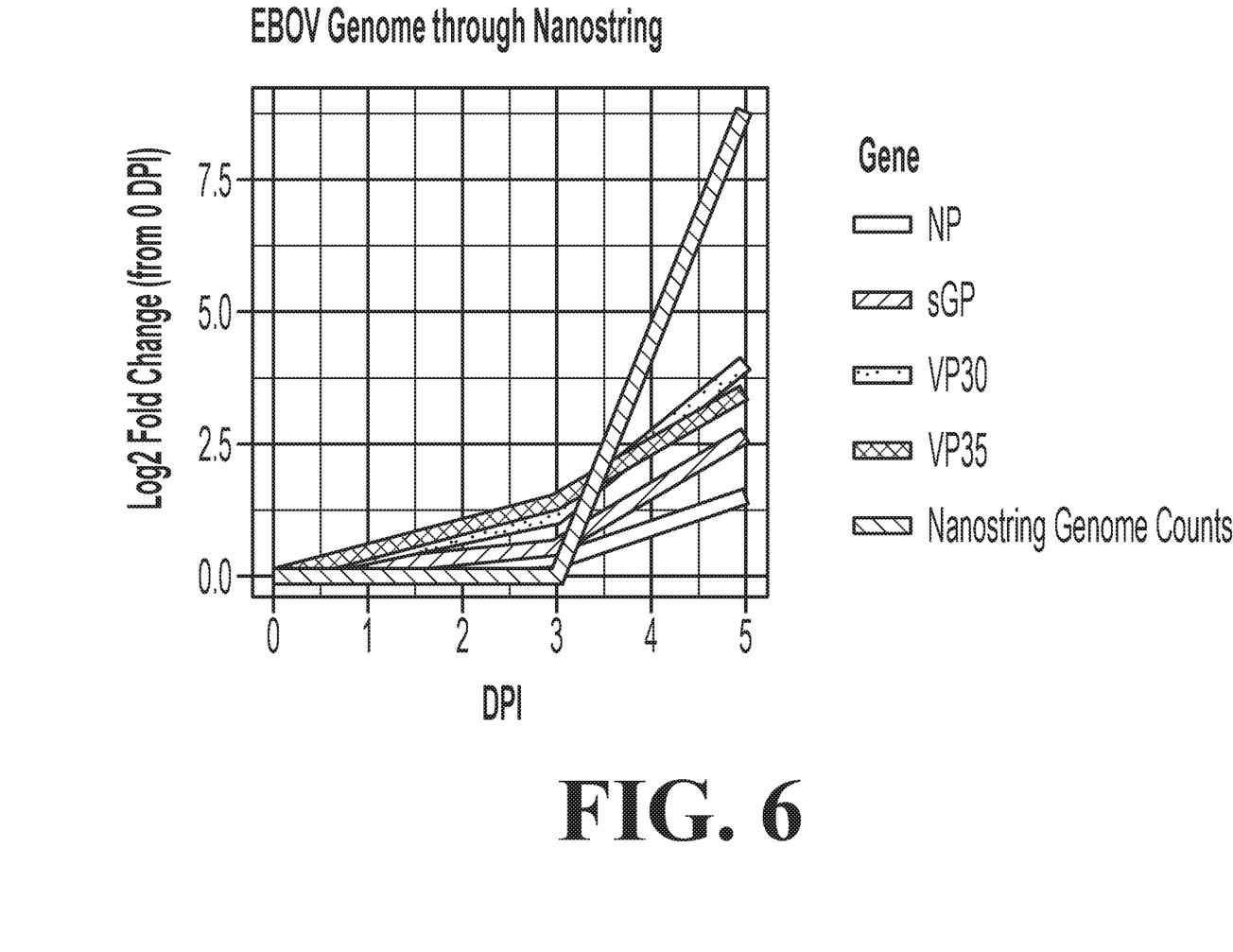
FIG. 6 illustrates a graphical representation of a presence of Ebola Virus viral proteins in a biological sample according to an example embodiment.

FIG. 6 illustrates a graphical representation of a presence of Ebola viral proteins in the samples tested. Each NP, sGP, VP 30, and VP 35 line represents proteomic results in the samples. The nanostring genome counts line represents RNA analysis using nanostring genome count. As shown in FIG. 6, the proteomic data showed that multiple EBOV viral proteins, such as NP, sGP, VP30 and VP35, were present in the samples and gradually increased in abundance the more days the subject had been exposed to the virus. VP30 and VP35 also showed significant upregulation at 3 days post exposure.

Thus, in accordance with example embodiments herein, a method for a pre-symptomatic diagnosis of a viral illness in a subject may be provided. The method may include obtaining a biological sample that includes at least one peripheral blood mononuclear cell from a subject prior to the subject experiencing any symptoms associated with the viral illness. The method may further include extracting proteins from the biological sample. The method may also include analyzing the extracted proteins, via mass spectrometry, for the presence of a predefined viral protein biomarker associated with the viral illness. If the predefined viral protein biomarker is present, the subject is diagnosed with the viral illness prior to experiencing the symptoms associated with the viral illness.

In some embodiments, additional optional steps and/or features may be included or the steps/features described above may be modified or augmented. Each of the additional features, steps, modifications, or augmentations may be practiced in combination with the steps/features above and/or in combination with each other. Thus, some, all or none of the additional features, steps, modifications, or augmentations may be utilized in some embodiments. Some example additional optional features, steps, modifications, or augmentations are described below, and may include, for example, that the viral illness may be Ebola Virus Disease. Alternatively or additionally, the predefined viral protein biomarker may be any one of Ebola Virus Disease viral proteins, the Ebola Virus Disease viral proteins including nucleoprotein, VP30, VP35, VP40, or glycoprotein. Alternatively or additionally, the predefined viral protein biomarker may be a plurality of biomarkers, the plurality of biomarkers being at least two of nucleoprotein, VP40, VP30, VP35, or glycoprotein. Alternatively or EV, obtaining the biological sample may include obtaining the biological sample within five days from suspected exposure to the viral illness. Alternatively or additionally, the method may include stimulating the biological sample by adding a predetermined amount of reagent to the biological sample to produce a mixture, where the reagent is configured to having a binding reaction in a presence of a predefined viral protein biomarker associated with the viral illness and then analyzing the mixture to determine if the reagent had the binding reaction, where if the binding reaction is detected, the subject is diagnosed with the viral illness prior to the subject experiencing symptoms of the viral illness. Alternatively or additionally, the reagent may include a first reagent and a second reagent, where the first reagent is configured to having the binding reaction in the presence of nucleoprotein and the second reagent is configured to have the binding reaction in the presence of VP30 or VP35. Alternatively or additionally, the stimulation of the biological sample may include incubating the biological sample and the antigen for a predetermined time. Alternatively or additionally, the predetermined time for incubating the biological sample may be for a period of 1-5 hours.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe exemplary embodiments in the context of certain exemplary combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. In cases where advantages, benefits or solutions to problems are described herein, it should be appreciated that such advantages, benefits and/or solutions may be applicable to some example embodiments, but not necessarily all example embodiments. Thus, any advantages, benefits or solutions described herein should not be thought of as being critical, required or essential to all embodiments or to that which is claimed herein. Although specific terms are employed herein, they are used in a generic and descriptive sense only and not for purposes of limitation.

What is claimed is:

1. A method of detecting a predefined viral protein biomarker in a subject, the method comprising:
  a) obtaining a biological sample comprising at least one peripheral blood mononuclear cell from the subject prior to the subject experiencing any symptoms associated with the viral illness;
  b) extracting proteins from the biological sample and digesting the extracted proteins to form protein fragments; and
  c) analyzing the protein fragments and detecting whether the predefined viral protein biomarker is present in the biological sample via mass spectrometry prior to the subject experiencing any symptoms associated with a viral illness, wherein the biological sample is obtained within 5 days from a suspected exposure to the viral illness; and the viral illness is Ebola virus disease.

2. The method of claim 1, wherein the predefined viral protein biomarker is any one of Ebola Virus Disease viral proteins, the Ebola Virus Disease viral proteins comprising nucleoprotein, VP30, VP35, VP40, or glycoprotein.

3. The method of claim 2, wherein the predefined viral protein biomarker is a plurality of biomarkers, the plurality of biomarkers being at least two of nucleoprotein, VP40, VP30, VP35, or glycoprotein.

4. The method of claim 1, wherein the viral illness is Ebola Virus Disease and the predefined viral protein biomarker is VP30, VP35, or both.

5. A method of detecting a predefined viral protein biomarker in a subject, the method comprising:
   a) obtaining a biological sample comprising at least one peripheral blood mononuclear cell from the subject prior to the subject experiencing any symptoms associated with a viral illness;
   b) stimulating the biological sample, the stimulation of the biological sample comprising contacting the biological sample with a predetermined amount of reagent, wherein the reagent is configured to have a binding reaction in a presence of the predefined viral protein biomarker; and
   c) detecting whether the predefined viral protein biomarker is present in the biological sample prior to the subject experiencing the symptoms by detecting the binding reaction between the predefined viral protein biomarker and the reagent, wherein the biological sample is obtained within 5 days from a suspected exposure to the viral illness ; and the viral illness is Ebola virus disease.

6. The method of claim 5, wherein the predefined viral protein biomarker is any one of Ebola Virus Disease viral proteins, the Ebola Virus Disease viral proteins comprising nucleoprotein, VP35, VP40, VP30, or glycoprotein.

7. The method of claim 6, wherein the predefined viral protein biomarker is a plurality of biomarkers, the plurality of biomarkers being at least two of nucleoprotein, VP40, VP35, VP30, or glycoprotein.

8. The method of claim 7, wherein the reagent comprises a first reagent and a second reagent, wherein the first reagent is configured to have the binding reaction in the presence of nucleoprotein and the second reagent is configured to have the binding reaction in the presence of VP30 or VP35.

9. The method of claim 5, wherein the stimulation of the biological sample further comprises incubating the biological sample and an antigen for a predetermined time.

10. The method of claim 9, wherein the predetermined time for incubating the biological sample is for a period of 1-5 hours.

11. The method of claim 5, wherein obtaining the biological sample comprises isolating the at least one peripheral blood mononuclear cell from other components of the biological sample.

12. The method of claim 5, wherein obtaining the biological sample comprises fractioning the biological sample.

13. The method of claim 5, wherein the viral illness is Ebola Virus Disease and the predefined viral protein biomarker is VP30, VP35, or both.

14. The method of claim 13, wherein the predefined viral protein biomarker comprises VP30 and VP35.

15. The method of claim 13, wherein obtaining a biological sample comprises (i) obtaining an initial biological sample prior to the subject experiencing any symptoms associated with Ebola Virus Disease and analyzing the mixture to determine a first assay of VP30, VP35, or both, (ii) obtaining a second biological sample from about 1 to about 3 days after obtaining the initial biological sample and determining a second assay of VP30, VP35, or both, and (iii) comparing the second assay to the first assay and diagnosing the subject with Ebola Virus Disease in response to the second assay being larger than the first assay.

16. The method of claim 15, wherein obtaining the second biological sample occurs prior to the subject experiencing any symptoms associated with Ebola Virus Disease.

\* \* \* \* \*